(12) United States Patent
Ohtsuki et al.

(10) Patent No.: US 9,748,151 B2
(45) Date of Patent: Aug. 29, 2017

(54) METHOD FOR EVALUATING SEMICONDUCTOR SUBSTRATE

(71) Applicant: SHIN-ETSU HANDOTAI CO., LTD., Tokyo (JP)

(72) Inventors: Tsuyoshi Ohtsuki, Annaka (JP); Hiroshi Takeno, Annaka (JP)

(73) Assignee: SHIN-ETSU HANDOTAI CO., LTD., Tokyo (JP)

(*) Notice: Subject to any disclaimer, the term of this patent is extended or adjusted under 35 U.S.C. 154(b) by 0 days.

(21) Appl. No.: 15/117,537

(22) PCT Filed: Feb. 23, 2015

(86) PCT No.: PCT/JP2015/000846
§ 371 (c)(1),
(2) Date: Aug. 9, 2016

(87) PCT Pub. No.: WO2015/141135
PCT Pub. Date: Sep. 24, 2015

(65) Prior Publication Data
US 2016/0365293 A1   Dec. 15, 2016

(30) Foreign Application Priority Data
Mar. 17, 2014  (JP) ................................. 2014-053585

(51) Int. Cl.
*H01L 21/66* (2006.01)
*H01L 21/324* (2006.01)
(Continued)

(52) U.S. Cl.
CPC ......... *H01L 22/24* (2013.01); *G01N 23/2254* (2013.01); *H01L 21/2686* (2013.01);
(Continued)

(58) Field of Classification Search
CPC combination set(s) only.
See application file for complete search history.

(56) References Cited

U.S. PATENT DOCUMENTS

2005/0272228 A1   12/2005  Ito et al.
2009/0023276 A1    1/2009  Suguro
(Continued)

FOREIGN PATENT DOCUMENTS

JP   2005-347704 A   12/2005
JP   2009-027027 A    2/2009
(Continued)

OTHER PUBLICATIONS

Oct. 18, 2016 Office Action issued in Japanese Patent Application No. 2014-053585.
(Continued)

*Primary Examiner* — Mamadou Diallo
(74) *Attorney, Agent, or Firm* — Oliff PLC

(57) ABSTRACT

The present invention provides a method for evaluating a semiconductor substrate subjected to a defect recovery heat treatment to recover a crystal defect in the semiconductor substrate having the crystal defect, flash lamp annealing is performed as the defect recovery heat treatment, and the method includes steps of measuring the crystal defect in the semiconductor substrate, which is being recovered, by controlling treatment conditions for the flash lamp annealing and analyzing a recovery mechanism of the crystal defect on the basis of a result of the measurement. Consequently, the method for evaluating a semiconductor substrate which enables evaluating a recovery process of the crystal defect is provided.

11 Claims, 1 Drawing Sheet

(51) Int. Cl.
   *G01N 23/225* (2006.01)
   *H01L 21/265* (2006.01)
   *H01L 21/268* (2006.01)
   *H01L 21/322* (2006.01)

(52) U.S. Cl.
   CPC ...... *H01L 21/26513* (2013.01); *H01L 21/322* (2013.01); *H01L 21/324* (2013.01); *G01N 2223/3106* (2013.01); *G01N 2223/6116* (2013.01)

(56) References Cited

U.S. PATENT DOCUMENTS

2012/0012983 A1* 1/2012 Ono .................. C30B 29/06
  257/607
2012/0119323 A1* 5/2012 Akiyama ............ H01L 21/265
  257/507
2014/0273328 A1* 9/2014 Sagara ............. H01L 27/14698
  438/57
2014/0370645 A1* 12/2014 Yamaguchi ....... H01L 27/14698
  438/72

FOREIGN PATENT DOCUMENTS

| | | |
|---|---|---|
| JP | 2010-287778 A | 12/2010 |
| JP | 2013-051317 A | 3/2013 |
| JP | 2013-131591 A | 7/2013 |

OTHER PUBLICATIONS

May 26, 2015 International Search Report issued in International Patent Application No. PCT/JP2015/000846.
Sep. 29, 2016 International Preliminary Report on Patentability issued in Patent Application No. PCT/JP2015/000846.

* cited by examiner

METHOD FOR EVALUATING SEMICONDUCTOR SUBSTRATE

TECHNICAL FIELD

The present invention relates to a method for evaluating a semiconductor substrate.

BACKGROUND ART

Miniaturization has been advance to realize LSI high performance, and a gate length has been reduced. Since the gate length has been reduced, a diffusion depth of a source/drain region must be decreased. For example, in case of a device (a transistor) having a gate length of approximately 30 nm, a source/drain portion has a diffusion length of approximately 15 nm, and very shallow diffusion is required.

In conventional examples, to form such a diffusion layer, ion implantation is used, and a method for implanting, e.g., $B^+$ or $BF_2^{++}$ at very low acceleration of 0.2 to 0.5 keV is adopted. However, atoms which have undergone the ion implantation cannot reduce a resistance thereof as they are. Further, in a region where the ion implantation has been carried out, point defects such as interstitial silicon or atomic vacancies are produced in a silicon substrate.

Thus, after the ion implantation, annealing is performed to activate the atoms (reduce the resistance) and recover the defects, but the ion-implanted atoms diffuse and an impurity distribution spreads due to this annealing. Furthermore, there is also known a phenomenon that impurity diffusion is accelerated by not only the annealing but also the point defects produced due to the ion implantation.

To enable formation of a shallow p-n junction of 10 nm or less in a transverse direction immediately below an ion implantation mask at a depth of 15 nm or less even though the spread of diffusion is taken into consideration, an annealing method of applying high energy in a very short time has been examined and adopted (see, e.g., Patent Literature 1).

As this method for annealing, there is, e.g., annealing which uses a flash lamp having a rare gas such as xenon enclosed therein. This lamp is a method for applying high energy of tens of $J/cm^2$ or more as pulse light of 0.1 to 100 milliseconds. Thus, activation can be carried out without substantially changing the impurity distribution formed by the ion implantation.

However, since this high energy is used, it can be considered that thermal stress in the silicon substrate increases and damage such as cracks or slips of the silicon substrate are caused, and an examination for this has been actually conducted.

For example, Patent Literature 2 has a description in which, to form a shallow impurity diffusion region without causing damage in a semiconductor substrate, materials having a material which serves as an acceptor or a donor to the semiconductor substrate and a material which does not serve as the acceptor or the donor to the semiconductor substrate are implanted into the semiconductor substrate.

It is known that crystal defects such as point defects are recovered by a heat treatment as described above. However, particulars of this recovery process are not known, and hence performing precise defect control is difficult in conventional methods.

CITATION LIST

Patent Literatures

Patent Literature 1: Japanese Unexamined Patent Publication No. 2005-347704

Patent Literature 2: Japanese Unexamined Patent Publication No. 2009-027027

SUMMARY OF INVENTION

Technical Problem

In view of the problem, it is an object of the present invention to provide a method for evaluating a semiconductor substrate which can evaluate a recovery process of crystal defects.

Solution to Problem

To achieve the object, the present invention provides a method for evaluating a semiconductor substrate subjected to a defect recovery heat treatment to recover a crystal defect in the semiconductor substrate having the crystal defect, flash lamp annealing being performed as the defect recovery heat treatment, the method including steps of:

measuring the crystal defect in the semiconductor substrate, which is being recovered, by controlling treatment conditions for the flash lamp annealing; and analyzing a recovery mechanism of the crystal defect on the basis of a result of the measurement.

Such a method for evaluating a semiconductor substrate enables accurately evaluating the recovery process of the crystal, defect. In particular, the defect recovery heat treatment is performed in the form of the flash lamp annealing (FLA), a state in the process of recovering the crystal defect can be frozen and measured by controlling the conditions for this treatment, and hence behavior of the crystal defect in the recovery process can be grasped. Grasping this defect behavior enables evaluating which defect recovery heat treatment is effective for execution of the precise defect control.

Further, at the step of performing the measurement, a measurement is preferably further performed after recovery of the crystal defect.

Since such a method for evaluating a semiconductor substrate enables comparing states of the semiconductor substrate during and after the recovery of the crystal defect with each other, and hence the recovery process of the crystal defect can be evaluated in further detail.

Furthermore, the treatment condition for the flash lamp annealing to be changed is preferably a heat treatment time or irradiation energy.

Such a method for evaluating a semiconductor substrate enables observing the defect recovery behavior in further detail. In particular, changing a heat treatment time enables observing the defect recovery behavior with time.

Moreover, the crystal defect is preferably an ion implantation defect produced by implanting ions into the semiconductor substrate.

The present invention is particularly suitable for evaluating the recovery process of the ion implantation defect such as a point defect produced by implanting ions into the semiconductor substrate.

Additionally, at the step of performing the measurement, a state before an emission line produced due to the crystal defect provided by a luminescence method is annihilated is preferably measured at least once, and also a state after the emission line is annihilated is preferably measured.

Such a method for evaluating a semiconductor substrate enables analyzing under which treatment conditions how the crystal defect in the semiconductor substrate is annihilated at a subsequent step (a step of analyzing a recovery mechanism).

At this time, the luminescence method is preferably a cathode luminescence method.

In the present invention, for example, it is preferable to use such a method to evaluate a silicon semiconductor substrate.

Further, at the step of performing the analysis, the recovery mechanism is preferably analyzed by observing a change in intensity of the emission line.

According to the evaluation method having such an analyzing step, the defect recovery behavior can be observed in more detail, and hence the recovery mechanism can be analyzed in further detail.

Furthermore, the semiconductor substrate is preferably a silicon semiconductor substrate.

The present invention is particularly preferable for evaluating the defect recovery process of the silicon semiconductor substrate having the crystal defect.

Advantageous Effects of Invention

The method for evaluating a semiconductor substrate according to the present invention enables accurately evaluating the recovery process of the crystal defect. In particular, since an ongoing process of the recovery of the crystal defect can be measured by performing the flash lamp annealing as the defect recovery heat treatment, behavior of the crystal defect during the recovery process can be grasped. Furthermore, when the semiconductor substrate is measured by using the luminescence method, the behavior of the crystal defect during the recovery process can be grasped in further detail. Grasping this defect behavior enables evaluating which defect recovery heat treatment is effective for execution of precise defect control.

DESCRIPTION OF EMBODIMENTS

Figure 1:
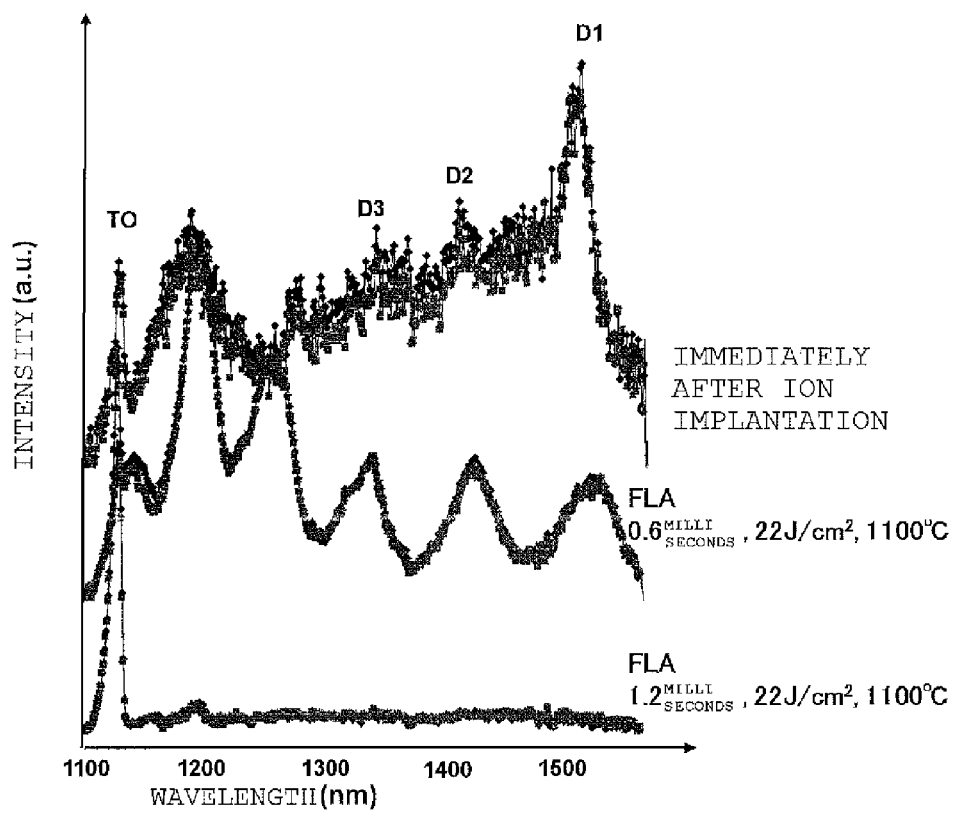
FIG. 1 shows CL spectrums provided as a result of measuring a silicon semiconductor substrate immediately after ion implantation, during recovery of a crystal defect, and after the recovery of the crystal defect based on a cathode luminescence (CL) method, respectively.

The present invention will now be more specifically described hereinafter.

As described above, a method for evaluating a semiconductor substrate which enables evaluating a recovery process of a crystal defect has been demanded.

As a result of intensive studies, the present inventors have found out that the problem can be solved by a method for evaluating a semiconductor substrate subjected to a defect recovery heat treatment to recover a crystal defect in the semiconductor substrate having the crystal defect, flash lamp annealing being performed as the defect recovery heat treatment, the method including steps of:

measuring the crystal defect in the semiconductor substrate, which is being recovered, by controlling treatment conditions for the flash lamp annealing; and analyzing a recovery mechanism of the crystal defect on the basis of a result of the measurement, thereby bringing the method for evaluating a semiconductor substrate according to the present invention to completion.

Although an embodiment of the present invention will now be specifically described hereinafter, the present invention is not restricted thereto.

[Step of Preparing Semiconductor Substrate Having Crystal Defect]

First, a silicon semiconductor substrate, e.g., a P-type silicon wafer having a dopant such as boron doped therein is prepared. Then, an impurity diffusion layer is formed on a surface of this wafer. The impurity diffusion layer can be formed by ion-implanting the dopant, e.g., boron. An ion implantation defect such as a point defect is formed in the silicon semiconductor substrate by this ion implantation.

[Step of Measuring Crystal Defect]

Then, the crystal defect in the semiconductor substrate subjected to a defect recovery heat treatment is measured. In the present invention, the defect recovery heat treatment is performed in the form of flash lamp annealing, and the crystal defect in the semiconductor substrate which is in the process of recovery is measured by controlling treatment conditions for the flash lamp annealing. According to the present invention, since a state of the crystal defect during the recovery can be measured, and hence behavior of the crystal defect in the process of recovery which is not revealed in the conventional examples can be grasped.

As a method of the defect recovery heat treatment in the present invention, there is, e.g., annealing using a flash lamp having a rare gas such as xenon enclosed therein, but the flash lamp annealing is not restricted thereto, and any method which applies high energy in a very short time can suffice.

Moreover, the crystal defect in the semiconductor substrate in the process of recovery may be measured only once, but the annealing may be carried out under a plurality of treatment conditions, which is use of a flash lamp, and the measurement may be performed more than once. When the measurement is performed more than once, the behavior of the crystal defect can be grasped in more detail.

At this time, it is preferable to likewise perform the measurement after the recovery of the crystal defect at the step of carrying out the measurement. Consequently, a state of the semiconductor substrate during the recovery of the crystal defect can be compared with the counterpart after the recovery of the same, and hence the recovery process of the crystal defect can be evaluated in more detail.

Additionally, at the step of performing the measurement, it is preferable to likewise measure the crystal defect in the semiconductor substrate before effecting the defect recovery heat treatment. Consequently, it is possible to compare states of the semiconductor substrate immediately after production of the crystal defect, during the recovery of the crystal defect, and after the recovery of the crystal defect with each other, and hence the recovery process of the crystal defect can be evaluated in more detail.

At this time, the treatment condition for the flash lamp annealing to be changed is preferably a heat treatment time or irradiation energy. Consequently, the defect recovery behavior can be observed in more detail. In particular, the defect recovery behavior can be observed with time by changing a heat treatment time.

As a measuring method which can be adopted in the step of performing the measurement, there is, e.g., a luminescence method such as a cathode luminescence (CL) method.

In this case, at the step of performing the measurement, it is preferable to measure at least once a state before an emission line (for example, a D1, D2, or D3 line produced due to a dislocation provided by the CL method) produced due to the crystal defect provided by the luminescence method is annihilated, and to further measure a state after the emission line is annihilated. Consequently, at a later-described step of analyzing a recovery mechanism, it is possible to analyze under which treatment conditions how the crystal defect in the semiconductor substrate is annihilated.

Among the luminescence methods, it is particularly preferable to adopt the cathode luminescence method at the time of measuring the silicon semiconductor substrate. According to the cathode luminescence method, it is possible to evaluate a stress/damage distribution, a defect distribution, and a carrier distribution of a sample with high spatial resolution while using an electron beam as a probe. The cathode luminescence means light emission in an ultraviolet/visible/near-infrared region emitted when the electron beam is applied to the sample.

Although the mechanism of light emission in this CL method varies depending on materials, in case of a semiconductor, there are (1) generation of an electron-hole pair, (2) diffusion of a carrier, and (3) radiative recombination. In case of silicon, a TO phonon line (a TO line) corresponding to a band gap (approximately 1.1 eV) is intensively observed. This is an interband transition involving phonon emission since silicon is an indirect transition semiconductor. When a crystal defect or an impurity forms an energy level in a band gap, light emission (a D1, D2, or D3 line or the like) via this defect or impurity occurs besides the interband transition light emission.

As regards an apparatus, a scanning electron microscope (SEM) is generally used as an electron beam source, and it is preferable to use an apparatus including a detector/spectroscope which detects light emission from a sample and a mechanism for, e.g., stage cooling to suppress lattice vibration and provide light emission intensity. As can be understood from an outline of the apparatus using the SEM as the electron beam source, the CL method is characterized in that a comparison with an SEM image is possible, an emission spectrum with a wide wavelength can be provided, and a depth analysis is possible by changing high resolution and an acceleration voltage.

Here, a description will now be given as to a case where the defect recovery heat treatment for recovery of a defect and activation is performed to the silicon semiconductor substrate having the crystal defect, and then CL spectrums (emission spectrums) are provided by using the cathode luminescence method. FIG. 1 shows CL spectrums provided as a result of measuring the silicon semiconductor substrate immediately after the ion implantation, during the recovery of the crystal defect, and after the recovery of the crystal defect based on the cathode luminescence method, respectively. In FIG. 1, an axis of ordinate represents emission intensity, and an axis of abscissa represents a wavelength. As shown in FIG. 1, the defect recovery process can be gradually measured by changing a heat treatment time of the flash lamp annealing.

[Step of Analyzing Recovery Mechanism]

Subsequently, on the basis of a result of the measurement, a recovery mechanism of the crystal defect is analyzed. In the present invention, behavior of the crystal defect in the recovery process can be grasped by measuring the crystal defect in the semiconductor substrate which is being recovered as described above, and the recovery mechanism can be analyzed. When the semiconductor substrate is further measured immediately after the ion implantation or after the recovery of the defect at the step of performing the measurement, the recovery mechanism can be analyzed in more detail at this step.

When the luminescence method, e.g., the cathode luminescence method is used at the step of performing the measurement, it is preferable to analyze the recovery mechanism by observing changes in intensity of the emission line provided by the luminescence method. As the defect recovery heat treatment advances, the crystal defect continues to recover, and hence the intensity of the emission line caused due to the crystal defect provided by the luminescence method is also relatively decreased. Thus, it is possible to evaluate under which treatment conditions how the crystal defect is annihilated or whether the crystal defect can be assuredly prevented from staying by observing the intensity of the emission line.

Here, the method for analyzing the recovery mechanism from the CL spectrums in FIG. 1 will now be described. As shown in FIG. 1, immediately after the ion implantation, the D1, D2, and D3 lines and the like caused due to dislocation are observed besides the TO line arising from band edge emission of silicon, and hence complicated spectrums are shown. However, as the annealing advances, the crystal defect continues to recover, and hence characteristic emission differs. That is, the intensity of the emission line caused due to the crystal defect is relatively decreased. When the recovery of the crystal defect is achieved, characteristic emission disappears. When the behavior of the defect is analyzed from the characteristic emission behavior, the semiconductor substrate subjected to the defect recovery heat treatment can be evaluated.

According to the present invention, a state in the defect recovery process can be frozen by using the flash lamp annealing, and the defect behavior which cannot be observed by the conventional annealing method can be grasped. Thus, it is possible to evaluate which defect recovery heat treatment is effective for execution of precise defect control. Further, since the defect recovery process can be gradually measured, treatment conditions such as an optimum heat treatment time or irradiation energy can be examined in accordance with each semiconductor substrate to be used.

[Use Application of Present Invention]

The present invention is preferable for evaluation of a recovery process of a crystal defect in the semiconductor substrate, especially an ion implantation defect caused at the time of forming a junction. In particular, it is preferable for evaluation of a defect recovery process (defect behavior) when a defect recovery heat treatment is applied to a semiconductor substrate subjected to high-concentration ion implantation like a source/drain, a gate electrode, or a well. Thus, the present invention can be adapted to manufacture of a semiconductor substrate having an impurity diffusion layer formed on a surface thereof.

EXAMPLES

The present invention will now be more specifically described hereinafter with reference to examples and comparative examples, but the present invention is not restricted to these examples.

[Relationship Between Defect Recovery Behavior and Heat Treatment Time]

Example 1

As a sample, an N-type silicon wafer which has phosphor doped therein and has a diameter of 200 mm was used. This silicon wafer has a resistivity of 10 Ω·cm. Boron was ion-implanted into this wafer with 10 keV and $1\times10^{13}$ atoms/cm$^2$. Then, as shown in FIG. 1, a CL spectrum of the wafer immediately after the ion implantation was first obtained by using the cathode luminescence method. Subsequently, flash lamp annealing using a xenon lamp as a light source was performed to this wafer at 550° C. of preliminary heating. At this time, the annealing was performed under two types of treatment conditions (irradiation energy of 22 J/cm$^2$, an irradiation time of 0.6 milliseconds, an irradiation temperature of 1100° C.; and irradiation energy of 22 J/cm$^2$, an irradiation time of 1.2 milliseconds, an irradiation temperature of 1100° C.). Then, as shown in FIG. 1, CL spectrums of the wafer after performing the annealing under the two types of treatment conditions were obtained, respectively.

FIG. 1 shows CL spectrums representing a recovery process of a crystal defect provided by FLA after the ion implantation. It is possible to see the process in which the emission center is decreased as the annealing advances immediately after the ion implantation as described above. Immediately after the ion implantation, disturbance in crystallinity occurs, intensity of the CL spectrums (TO lines) is weak, and many emission defects are observed. When the FLA is performed for a short time, light emission (a D1 line to a D3 line) caused due to the crystal defect in light emission observed in the CL spectrums is reduced as compared with that after the ion implantation, and further performing the annealing results in observation of no characteristic emission. As described above, in the present invention, the defect recovery behavior can be observed with time. Consequently, the recovery process of the crystal defect in the semiconductor substrate can be evaluated.

[Difference in CL Spectrum Provided by Annealing Technique]

Example 2: Evaluation Method Using Flash Lamp Annealing

As a sample, an N-type silicon wafer which has phosphor doped therein and has a diameter of 200 mm was used. This silicon wafer has a resistivity of 10 Ω·cm. Boron was ion-implanted into this wafer with 10 keV and $5\times10^{13}$ atoms/cm$^2$, and flash lamp annealing (annealing conditions are irradiation energy of 22 J/cm$^2$, 1.2 milliseconds, and an irradiation temperature of 1100° C.) using a xenon lamp as a light source was performed to this wafer at 550° C. of preliminary heating. Then, an ion implantation defect was evaluated.

Comparative Example 1: Evaluation Method Using RTA Treatment

As a sample, an N-type silicon wafer which has phosphor doped therein and has a diameter of 200 mm was used. This silicon wafer has a resistivity of 10 Ω·cm. Boron was ion-implanted into this wafer with 10 keV and $5\times10^{13}$ atoms/cm$^2$, and a rapid-heating and rapid-cooling heat treatment (an RTA treatment) was performed at 1000° C./30 seconds. Then, an ion implantation defect was evaluated.

Figure 2:
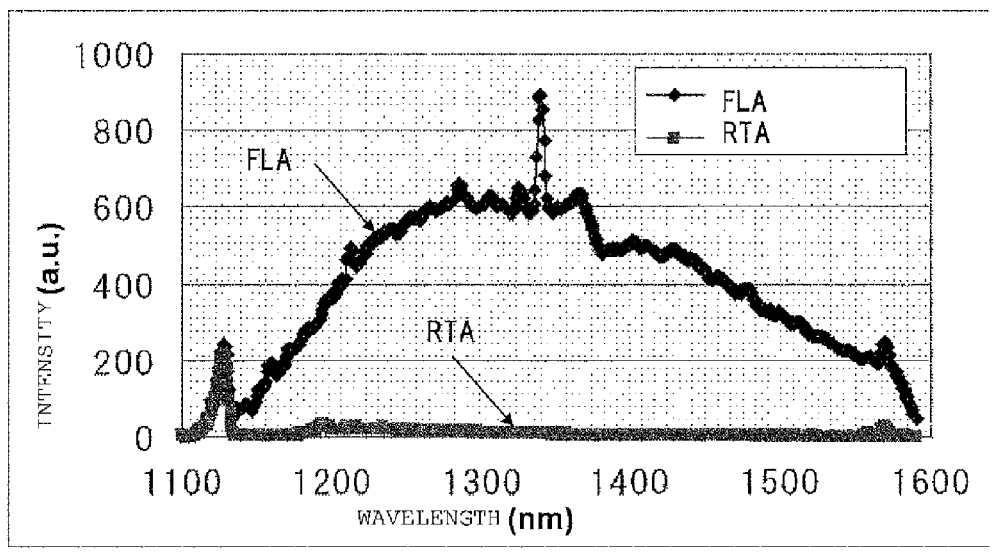
FIG. 2 shows CL spectrums provided as a result of measuring a silicon semiconductor substrate subjected to a defect recovery heat treatment in the form of flash lamp annealing and a silicon semiconductor substrate subjected to the same in the form of a rapid-heating and rapid-cooling heat treatment by using the CL method, respectively.

In Example 2 and Comparative Example 1, the ion implantation defects were first evaluated on the basis of observation using a transmission electron microscope (TEM), but no defect was observed with the TEM in regions where the ion implantation was performed. Then, as shown in FIG. 2, an evaluation was performed by using the cathode luminescence. FIG. 2 shows CL spectrums provided as a result of measuring the silicon semiconductor substrate subjected to the defect recovery heat treatment based on the flash lamp annealing and the silicon semiconductor substrate subjected to the rapid-heating and rapid-cooling heat treatment by the CL method, respectively. In FIG. 2, an axis of ordinate represents emission intensity, and an axis of abscissa represents a wavelength. In Example 2, broad characteristic light emission is observed besides a TO line (corresponding to a peak with a wavelength of approximately 1120 nm), but nothing was observed except the TO line in Comparative Example 1.

It can be considered that a difference in detection sensitivity between the evaluation based on the TEM observation and the evaluation using the CL is made for the following reason. That is, the TEM has a narrow observation region and is hard to capture a point detect as an image and, on the other hand, the CL has a large observation region (a depth direction in particular) since a scanning electron microscope (SEM) is used and detects the emission center of a deep level in principle, and hence the CL has higher detection sensitivity.

As described above, in Comparative Example 1 where the RTA treatment was performed as the defect recovery heat treatment, nothing was observed except the TO line, no defect recovery behavior was observed, and hence it was impossible to evaluate the recovery process of the crystal defect in the semiconductor substrate. On the other hand, in Example 2 where the flash lamp annealing was performed as the defect recovery heat treatment, many emission lines were observed besides the TO line. These emission lines represent the ion implantation defect behavior during the defect recovery process. Consequently, the recovery process of the crystal defect in the semiconductor substrate was successfully evaluated.

In Example 2 where an ion implantation amount is higher than that in Example 1 in particular, many emission defects were observed even under the same conditions (the irradiation energy of 22 J/cm$^2$, 1.2 milliseconds, and the irradiation temperature of 1100° C.). Thus, on the basis of the results of Examples 1 and 2, it was possible to evaluate that an optimum heat treatment time to recover the crystal defect differs when the defect recovery heat treatment is performed to the semiconductor substrates having different ion implantation amounts, respectively.

Furthermore, it can be understood from the results of Example 2 and Comparative Example 1 that the flash lamp annealing must be performed as the defect recovery heat treatment to evaluate the recovery process of the crystal defect (in particular, to measure the ongoing recovery).

It is to be noted that the present invention is not restricted to the foregoing embodiment. The foregoing embodiment is an illustrative example, and any example which has substantially the same configuration and exerts the same functions and effect as the technical scope described claims of the present invention is included in the technical scope of the present invention.

The invention claimed is:

1. A method for evaluating a semiconductor substrate subjected to a defect recovery heat treatment to recover a crystal defect in the semiconductor substrate having the crystal defect,
flash lamp annealing being performed as the defect recovery heat treatment,
the method comprising steps of:
measuring the crystal defect in the semiconductor substrate, which is being recovered, by controlling treatment conditions for the flash lamp annealing; and
analyzing a recovery mechanism of the crystal defect on the basis of a result of the measurement,
wherein, at the step of performing the measurement, a measurement is further performed after recovery of the crystal defect.

2. The method for evaluating a semiconductor substrate according to claim 1,
wherein the treatment condition for the flash lamp annealing to be changed is a heat treatment time or irradiation energy.

3. The method for evaluating a semiconductor substrate according to claim 1,
wherein the crystal defect is an ion implantation defect produced by implanting ions into the semiconductor substrate.

4. The method for evaluating a semiconductor substrate according to claim 2,
wherein the crystal defect is an ion implantation defect produced by implanting ions into the semiconductor substrate.

5. The method for evaluating a semiconductor substrate according to claim 1,
wherein, at the step of performing the measurement, a state before an emission line produced due to the crystal defect provided by a luminescence method is annihilated is measured at least once, and also a state after the emission line is annihilated is measured.

6. The method for evaluating a semiconductor substrate according to claim 2,
wherein, at the step of performing the measurement, a state before an emission line produced due to the crystal defect provided by a luminescence method is annihilated is measured at least once, and also a state after the emission line is annihilated is measured.

7. The method for evaluating a semiconductor substrate according to claim 3,
wherein, at the step of performing the measurement, a state before an emission line produced due to the crystal defect provided by a luminescence method is annihilated is measured at least once, and also a state after the emission line is annihilated is measured.

8. The method for evaluating a semiconductor substrate according to claim 4,
wherein, at the step of performing the measurement, a state before an emission line produced due to the crystal defect provided by a luminescence method is annihilated is measured at least once, and also a state after the emission line is annihilated is measured.

9. The method for evaluating a semiconductor substrate according to claim 5,
wherein the luminescence method is a cathode luminescence method.

10. The method for evaluating a semiconductor substrate according to claim 5,
wherein, at the step of performing the analysis, the recovery mechanism is analyzed by observing a change in intensity of the emission line.

11. The method for evaluating a semiconductor substrate according to claim 1,
wherein the semiconductor substrate is a silicon semiconductor substrate.

* * * * *